(12) United States Patent
Heinecke et al.

(10) Patent No.: US 6,927,315 B1
(45) Date of Patent: Aug. 9, 2005

(54) ADHESIVE COMPOSITE HAVING DISTINCT PHASES

(75) Inventors: Steven B. Heinecke, New Richmond, WI (US); Robert H. Menzies, Hudson, WI (US); Karen M. Bisbee, Maplewood, MN (US); Scott G. Norquist, St. Paul, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/364,506

(22) Filed: Jul. 30, 1999

(51) Int. Cl.[7] .............................. A61F 5/00; A61S 13/00
(52) U.S. Cl. .......................................... 602/41; 602/58
(58) Field of Search ................................ 424/443, 445, 424/448, 449, 269; 602/41–59; 604/336, 344

(56) References Cited

U.S. PATENT DOCUMENTS

| | | | |
|---|---|---|---|
| 2,736,721 A | 2/1956 | Dexter | 260/42 |
| RE24,906 E | 12/1960 | Ulrich | 206/59 |
| 3,365,315 A | 1/1968 | Beck et al. | 106/40 |
| 3,485,912 A | 12/1969 | Schrenk et al. | 264/171 |
| 3,645,835 A | 2/1972 | Hodgson | 161/146 |
| 3,792,945 A | 2/1974 | Randall | 425/132 |
| 4,138,193 A | 2/1979 | Olszewski et al. | 350/96.23 |
| 4,197,069 A | 4/1980 | Cloeren | 425/131.1 |
| 4,386,125 A | 5/1983 | Shiraki et al. | 428/36 |
| 4,454,192 A | 6/1984 | Suzuki | 428/294 |
| 4,464,157 A | 8/1984 | Benoit et al. | 493/211 |
| 4,499,896 A | 2/1985 | Heinecke | 128/156 |
| 4,521,359 A | 6/1985 | Tsien | 264/104 |
| 4,533,308 A | 8/1985 | Cloeren | 425/131.1 |
| 4,536,362 A | 8/1985 | Donaldson | 264/171 |
| 4,539,248 A | 9/1985 | Brockington et al. | 428/161 |
| 4,592,938 A | 6/1986 | Benoit | 428/35 |
| 4,598,004 A | 7/1986 | Heinecke | 428/40 |
| 4,646,731 A | 3/1987 | Brower | 128/156 |
| 4,650,817 A * | 3/1987 | Allen, Jr. et al. | 523/105 |
| 4,767,726 A | 8/1988 | Marshall | 501/33 |
| 4,770,490 A | 9/1988 | Gruenewald et al. | 350/96.23 |
| 4,773,408 A * | 9/1988 | Cilento et al. | 604/358 X |
| 4,784,815 A | 11/1988 | Cloeren et al. | 264/171 |
| 4,787,897 A | 11/1988 | Torimae et al. | 604/389 |
| 4,798,201 A | 1/1989 | Rawlings | 128/156 |
| 4,813,947 A | 3/1989 | Korpman | 604/389 |
| 4,816,316 A | 3/1989 | Robbins, III | 428/161 |
| 4,833,179 A | 5/1989 | Young et al. | 522/183 |
| 4,917,928 A | 4/1990 | Heinecke | 428/41 |
| 4,917,929 A | 4/1990 | Heinecke | 428/41 |
| RE33,353 E | 9/1990 | Heinecke | 428/40 |
| 5,057,097 A | 10/1991 | Gesp | 604/389 |
| 5,059,375 A | 10/1991 | Lindsay | 264/167 |

(Continued)

FOREIGN PATENT DOCUMENTS

| | | | | |
|---|---|---|---|---|
| EP | 0 437 944 A1 | 7/1991 | | A61F/13/02 |
| EP | 0 641 639 A1 | 3/1995 | | B29C/47/04 |

(Continued)

OTHER PUBLICATIONS

*Encyclopedia of Polymer Science and Engineering*, vol. 13, Poly(phenylene Ether) to Radical Polymerization, A Wiley-Interscience Publication, John Wiley & Sons, Copyright 1988, pp. 345–357.

(Continued)

*Primary Examiner*—Kim M Lewis
(74) *Attorney, Agent, or Firm*—Nancy M. Lambert (57) ABSTRACT

A conformable adhesive article for use as a sterile medical dressing is described. The article includes a breathable polymeric matrix, a plurality of phases, and an adhesive composition positioned on the polymeric matrix. The plurality of phases preferably provide reinforcement and stiffness to the article. The article permits transport of moisture across the breathable polymeric matrix, preferably at an Inverted water moisture vapor transmission rate of at least 300 $g/m^2/24$ hours.

33 Claims, 3 Drawing Sheets

U.S. PATENT DOCUMENTS

| | | | | |
|---|---|---|---|---|
| 5,079,066 A | | 1/1992 | Leseman et al. | 428/167 |
| 5,080,957 A | | 1/1992 | Leseman et al. | 428/167 |
| 5,100,672 A | * | 3/1992 | Gueret et al. | 424/449 |
| 5,110,530 A | | 5/1992 | Havens | 264/171 |
| 5,142,750 A | | 9/1992 | Dyer et al. | 26/29 |
| 5,145,544 A | | 9/1992 | Leseman et al. | 156/229 |
| 5,173,141 A | | 12/1992 | Leseman et al. | 156/244.15 |
| 5,209,971 A | | 5/1993 | Babu et al. | 428/343 |
| 5,217,794 A | | 6/1993 | Schrenk | 428/220 |
| 5,236,972 A | | 8/1993 | Reinhart | 523/122 |
| 5,298,310 A | | 3/1994 | Havens | 428/204 |
| 5,302,629 A | * | 4/1994 | Berejka | 523/111 |
| 5,316,703 A | | 5/1994 | Schrenk | 264/1.3 |
| 5,397,298 A | * | 3/1995 | Mazza et al. | 602/75 |
| 5,429,856 A | | 7/1995 | Krueger et al. | 604/370 |
| 5,461,134 A | | 10/1995 | Leir et al. | 528/14 |
| 5,462,708 A | | 10/1995 | Swenson et al. | 264/174.11 |
| 5,464,107 A | | 11/1995 | Koeniger | 215/12.2 |
| 5,468,428 A | | 11/1995 | Hanschen et al. | 264/483 |
| 5,520,629 A | | 5/1996 | Heinecke et al. | 602/57 |
| 5,531,855 A | | 7/1996 | Heinecke et al. | 156/252 |
| 5,589,122 A | | 12/1996 | Leonard et al. | 264/146 |
| 5,620,780 A | | 4/1997 | Krueger et al. | 428/179 |
| 5,656,167 A | * | 8/1997 | Martz | 210/490 |
| 5,656,352 A | | 8/1997 | Middleton | 428/131 |
| 5,660,922 A | | 8/1997 | Herridge et al. | 428/214 |
| 5,773,374 A | | 6/1998 | Wood et al. | 442/328 |
| 5,792,529 A | | 8/1998 | May | 428/36.2 |
| 5,800,903 A | | 9/1998 | Wood et al. | 428/152 |
| 5,849,325 A | | 12/1998 | Heinecke et al. | 424/443 |
| 5,876,745 A | * | 3/1999 | Muraoka et al. | 424/448 |
| 5,885,908 A | | 3/1999 | Jaeger et al. | 442/59 |
| 5,902,435 A | | 5/1999 | Meis et al. | 156/230 |
| 6,045,900 A | * | 4/2000 | Haffner et al. | 428/315.9 |
| 6,074,965 A | * | 6/2000 | Bodenschatz et al. | 428/295.4 |
| 6,103,152 A | | 8/2000 | Gehlsen et al. | 264/45.4 |
| 6,270,910 B1 | | 8/2001 | Jaeger et al. | 428/500 |
| 6,447,875 B1 | | 9/2002 | Norquist et al. | 428/107 |

FOREIGN PATENT DOCUMENTS

| | | | | |
|---|---|---|---|---|
| GB | 2 249 266 A | | 5/1992 | A61F/15/00 |
| GB | 2 249 266 | | 5/1992 | |
| JP | 6-293067 | | 10/1994 | B29C/55/02 |
| WO | WO 88/08787 | | 11/1988 | B32B/3/00 |
| WO | 88/08787 | * | 11/1988 | |
| WO | WO 93/07228 | | 4/1993 | C09J/7/02 |
| WO | WO 94/12134 | | 6/1994 | A61F/13/02 |
| WO | WO 95/16754 | | 6/1995 | C09J/7/02 |
| WO | WO 96/25469 | | 8/1996 | C09J/133/08 |
| WO | WO 96/34029 | | 10/1996 | C08G/18/61 |
| WO | WO 96/35458 | | 11/1996 | |
| WO | WO 97/23249 | | 7/1997 | A61L/15/58 |
| WO | WO 97/23577 | | 7/1997 | C09J/201/00 |

OTHER PUBLICATIONS

*Encyclopedia of Polymer Science and Technology*, "Plastics, Resins, Rubbers, Fibers", vol. 1, Interscience Publishers, a division of John Wiley & Sons, Copyright 1964, pp. 482–483 and 487–501.

*Handbook of Pressure Sensitive Adhesive Technology*, Second Edition, Van Nostrand Reinhold, New York, Copyright 1989, pp. 170–177.

Bird, R., et al., *Dynamics of Polymeric Liquids*, vol. 1, Fluid Mechanics, 2d ed., John Wiley & Sons, N.Y., 1987, p. 176.

Riccardo A.A. Muzzarelli, Fabio Tanfani, and Gianfranco Scarpini, "Chelating, Film–Forming, and Coagulating Ability of the Chitosan–Glucan Complex from *Aspergillus niger* Industrial Wastes", Institute of Biochemistry, Faculty of Medicine, University of Ancona, 1–60100 Ancona, Italy, Biotechnology and Bioengineering, vol. XXII, pp. 885–896 (1980) © 1980 John Wiley & Sons, Inc.

*Chelating, Film–Forming, and Coagulating Ability of the Chitosan–Glucan Complex from Aspergillus niger Industrial Wastes*, Riccardo A.A. Muzzarelli, Fabio Tanfani, and Gianfranco Scarpini, Institute of Biochemistry, Faculty of Medicine, University of Ancona, 1–60100 Ancona, Italy, Biotechnology and Bioengineering, vol. XXII, pp. 885–896 (1980) © 1980 John Wiley & Sons, Inc.

* cited by examiner

ADHESIVE COMPOSITE HAVING DISTINCT PHASES

FIELD OF THE INVENTION

The present invention is directed to conformable adhesive articles, including adhesive articles for use as sterile medical dressings. The invention is particularly directed to adhesive coated polymeric articles having high moisture vapor transmission rates. The articles of the present invention can be used for medical tapes, dressings, skin closures, drapes, and for other uses where a breathable conformable film is desired.

BACKGROUND OF THE INVENTION

Breathable films are widely used as protective layers over wounds, including dressings and surgical drapes. These films facilitate healing in a moist environment, act as a barrier to contamination from microorganisms, and allow for exchange of moisture to prevent excessive fluid buildup. Breathable films are preferably thin and flexible in order to permit high moisture transmission rates and to conform well to various irregular surfaces of a patient's body. Films fitting this description are available under a number of trade names, including TEGADERM™ produced by Minnesota Mining and Manufacturing Company of St. Paul, Minn.; BIOCLUSIVE™ produced by Johnson & Johnson Company of New Brunswick, N.J.; and OP-SITE™ produced by T.J. Smith & Nephew of Hull, England.

Unfortunately, the thin and flexible nature of breathable films can result in challenges when applying them to patients. These challenges often arise because dressings formed of adhesive coated film tend to wrinkle and adhere to themselves, interfering with smooth, aseptic application to a patient's skin. Various delivery systems have been proposed to address this challenge. One such delivery system is described in U.S. Pat. No. 5,531,855, which is directed to a releasable protective liner that covers the adhesive coated surface of the film. Unfortunately, when the liner is removed, the adhesive coated film often still wrinkles and adheres to itself.

An alternative delivery system includes a thin disposable frame on which the breathable film is releasably secured, such as the frames described in U.S. Pat. No. 5,520,629. As the film is applied to a wound on a patient, the frame is lifted away, leaving the film adhered to the patient. In such implementations, the film adheres more strongly to the patient than it does to the frame, thereby allowing for the release of the film from the frame. Although this method can work well, it poses some difficulty in making large breathable films, and can be difficult to produce.

Accordingly, a need exists for a thin, breathable film that can be applied to a wound in an easy and efficient manner. The film should allow for escape of moisture while protecting the wound from contamination. Such film should preferably be efficient and cost effective to produce, as well as easy to apply.

SUMMARY OF THE INVENTION

The invention is directed to a conformable adhesive article. The article is suitable for use as a sterile medical dressing, and includes a breathable polymeric matrix, a plurality of phases, and an adhesive composition positioned on or within at least a portion of the polymeric matrix. The breathable polymeric matrix allows for the escape of moisture across the adhesive article. The plurality of phases reinforce the polymeric matrix, thereby making a stronger matrix and permitting the matrix thickness to be minimized. The reinforcing phases can increase the stiffness of the article as measured by hand conformability and $F_{10}$ modulus conformability. The phases can also provide an increase in tensile strength of the article in order to make it less fragile during application and more durable after application.

A preferred use of the article is as an adhesive dressing applied over wounds. The dressing aids in the regulation of the amount of moisture in contact with the wound. In certain embodiments, the article maintains a sufficiently moist environment to prevent the underlying wound from dehydrating, without creating pools of liquid that can cause adhesive failure. The article preferably exhibits a satisfactory moisture vapor transmission rate while retaining its structural integrity in moist environments. This combination of breathability and strength allows for a superior breathable film that promotes the quick recovery of injuries, such as burns to a patient's skin.

The article preferably has enough modulus or stiffness to allow easy application to a patient, but is conformable enough to readily adapt to the shape of the covered area. In certain implementations, the article can be readily applied without the use of a release film, a retainer frame surrounding the article, or retainer handles at the ends of the article. However, the article can alternatively be used with these devices to aid in application to a patient.

The modulus of the article is preferably sufficient to aid in application, but not so great as to interfere with conformability to the patient. The article preferably exhibits increased modulus and tensile strength relative to existing breathable films suitable as wound dressings. The article typically has a conformability (Hand) of at least about 2 and less than about 10 in the direction parallel to the phases (in the cross-web direction when the phases are co-extruded in a down-web machine direction) and at least about 2 and less than 25 in the direction perpendicular to the phases (in the machine direction when the phases are co-extruded in a down-web machine direction).

In implementations where the film will be applied to generally flat surfaces, the film can have greater modulus than a film that would be applied to an irregular surface. Similarly, in implementations where the film will be applied to irregular surfaces or curved surfaces, then the film is preferably more flexible. However, even when the film has greater flexibility, such modulus is still preferably great enough to limit the amount of contact of the filming adhesive surface with itself.

The article should also typically have sufficient tensile strength to function as a satisfactory wound drape or dressing. In certain implementations the article has a tensile strength of at least about 8 N/cm width in the direction perpendicular to the phases (cross-web direction); and at least about 8 N/cm width, and preferably at least about 16 N/cm width in the direction parallel to the phases (machine direction). The tensile strength can vary depending upon the direction of the phases. The tensile strength is preferably more than 50 percent greater in the machine direction than a breathable polymeric matrix of the same thickness that does not contain a plurality of phases.

In order to allow transport of moisture away from a wound, the article typically has an inverted water moisture vapor transmission rate of at least about 300 g/m²/24 hours, preferably an inverted water moisture vapor transmission rate of at least about 1500 g/m²/24 hours, and more preferably an inverted water moisture vapor transmission rate of at least about 4000 g/m²/24 hours. The article typically has an upright water moisture vapor transmission rate of at least about 300 g/m²/24 hours, preferably an upright water moisture vapor transmission rate of at least about 600 g/m²/24 hours, and more preferably an upright water moisture vapor transmission rate of at least about 1000 g/m²/24 hours.

The breathable polymeric matrix can be formed of various materials. The matrix may include an elastomeric material and the plurality of phases can include a substantially non-elastic material. Alternatively, the breathable polymeric matrix and the plurality of phases can be formed of elastomeric materials, including a polymeric matrix comprising a thermoplastic polyurethane. The matrix can contain one layer or more than one layer, and the layers can comprise different materials or the same material. In specific implementations, the plurality of phases includes phases that are continuous in one direction, but discontinuous in another direction. The phases can be formed of a polymeric material different from the material used to form the polymeric matrix. The phases can have a significantly greater stiffness than the polymeric matrix and impart overall stiffness to the article by reinforcing the polymeric matrix. The phases preferably provide support and stiffness to the matrix without significantly reducing the conformability of the article.

In a specific implementation of the invention, the article comprises an extruded web containing a plurality of uniform, distinct phases positioned proximate the web. The phases are discontinuous in a cross-web direction. The phases positioned proximate the web may be entirely within the web, partially within the web, or adhered to the exterior of the web. The embedded phases preferably have a width uniform to within a coefficient of variation of less than 8 percent for three consecutive discontinuous phases. The width of these phases is measured in a cross-section of the web cut transverse (i.e., cross-web) to the machine direction (i.e., down-web) and is the largest dimension of the cross-section of the phases in the cross-web direction.

In certain implementations, the article is made into a roll good that facilitates easy dispensing of the breathable film. The roll good includes a breathable polymeric matrix having a first surface and a second surface, a plurality of substantially continuous phases retained proximate the polymeric matrix, and an adhesive composition positioned on at least a portion of the first surface of the polymeric matrix. The roll good can include perforations to form individual lengths of sterile medical dressings. These perforations provide tear lines that facilitate tearing of the roll good into shorter lengths.

The phases can be formed of a material compatible with the matrix to form a substantially integrated product with a strong interface between the matrix and the is phases. Alternatively, incompatible materials can be co-extruded to form the article. In such implementations, the phases are preferably encapsulated within the matrix in order to secure the phases in place. As used herein, "compatible" refers to the property of forming a strong interface between the two materials, while "incompatible" materials form a weak interface. Thus, one implementation of the invention provides for a plurality of phases substantially surrounded by the polymeric matrix and compatible with the matrix, and a second implementation provides for phases substantially surrounded by the polymeric matrix and not substantially compatible with the polymeric matrix.

Numerous alternative processes can be used to form the articles of the invention. These processes can alter the properties of the finished article, as well as the structure of the article. For example, the plurality of phases can be retained on the same surface of the polymer matrix as the adhesive composition, or can be retained on an opposite surface from the adhesive composition. When the plurality of phases are retained on the same surface as the adhesive composition, the phases can be intermediate the adhesive composition and the surface of the polymeric matrix or can be placed on top of the adhesive composition. The plurality of phases can be heat laminated between a polymeric matrix having at least two layers, extruded in two stages, solvent cast onto a release sheet; etc. A specific process suitable for forming the breathable article includes providing an extrudable material and an extrusion die, as described in U.S. patent application Ser. No. 09/365,286 entitled "Polymeric Articles Having Embedded Phases, filed on Jul. 30, 1999.

Other features and advantages of the invention will be apparent from the following description of the preferred embodiments thereof, and from the claims.

DETAILED DESCRIPTION OF THE INVENTION

The invention is directed to a conformable adhesive article for use as a sterile medical dressing. The article includes a breathable polymeric matrix, a plurality of phases proximate the matrix, and an adhesive composition positioned on at least a portion the polymeric matrix. The breathable polymeric matrix allows for escape of moisture across the adhesive article. This escape of moisture is particularly advantageous when the article is used as a medical dressing, drape, or other breathable article.

The plurality of phases reinforce the polymeric matrix, thereby strengthening the matrix and permitting the thickness of the matrix to be reduced. The reinforcement can also increase the modulus of the article so as to make it easier to apply to a patient, with reduced problems associated with adhesion of the article to itself. The phases can also provide an increase in tensile strength of the article in order to make it more durable. The modulus of the article is preferably not so great as to interfere with conformability to the patient. The article typically has a conformability (Hand) of at least about 2, and less than 10 in the direction parallel to the phases (measured such that the bar is parallel to the phases) and at least about 2 and less than 25 the direction perpendicular to the phases (measured such that the bar is perpendicular to the phases). The article preferably has a conformability (hand) of less than 5 in the direction parallel to the phases and less than 10 in the direction perpendicular to the phases.

A preferred use of the article is as an adhesive dressing for application over wounds. The dressing effectively regulates the amount of moisture in contact with the wound underlying the dressing. In certain embodiments, the article maintains a sufficiently moist environment to prevent the underlying wound from dehydrating, without creating pools of liquid that can cause adhesive failure. The article exhibits a high moisture vapor transmission rate while retaining its structural integrity in moist environments. The existence of phases of a second material within the matrix can promote formation of a stronger article than would otherwise be obtained without use of phases. In addition, the phases are preferably constructed and arranged such that moisture transport through the matrix is not greatly reduced.

In a preferred implementation, the article is stiff enough to allow easy application to a patient, but conformable enough to readily adapt to the shape of the covered area. The article can be readily applied to a patient without the use of a release film, a retainer frame surrounding the article, or retainer handles at the ends of the article.

The article should have sufficient tensile strength to function as a satisfactory wound drape or dressing. In certain implementations the article has a tensile strength of at least about 8 N/cm width in the direction perpendicular to the phases (cross-web direction when the matrix and phases are co-extruded); and at least about 8 N/cm width, and preferably at least about 16 N/cm width in the direction parallel to the phases (machine direction when the matrix and phases are co-extruded). The tensile strength can vary depending upon the direction of the phases, and the tensile strength is preferably more than 50 percent greater than a breathable polymeric matrix of the same thickness that does not contain a plurality of phases.

In order to allow transport of moisture away from a wound, the article typically has an inverted water moisture vapor transmission rate of at least about 300 g/m$^2$/24 hours, preferably an inverted water moisture vapor transmission rate of at least about 1500 g/m$^2$/24 hours, more preferably an inverted water moisture vapor transmission rate of at least about 4000 g/m$^2$/24 hours. The article typically has an upright water moisture vapor transmission rate of at least about 300 g/m$^2$/24 hours, preferably an upright water moisture vapor transmission rate of at least about 600 g/m$^2$/24 hours, more preferably an upright water moisture vapor transmission rate of at least about 1000 g/m$^2$/24 hours.

The article is preferably conformable to anatomical surfaces so that when the article is applied to a human or animal anatomical surface it conforms to the surface even when the surface is moved. Preferred articles are also conformable to animal or human anatomical joints. When the joint is flexed and then returned to its unflexed position, the article stretches to accommodate the flexing of the joint but is resilient enough to continue to conform to the joint when the joint is returned to its unflexed position. Generally the films are from 12 to 25 microns thick. Conformability is somewhat dependent upon thickness, thus the thinner the film the more conformable it is.

A measure of conformability is the $F_{10}$ modulus. The $F_{10}$ modulus should preferably be greater than about 1.8 N/cm and more preferably greater than about 1.4 N/cm. In preferred embodiments the wound dressings and drapes, films having an $F_{10}$ modulus upwards of 4.4 N/cm may be used. The $F_{10}$ modulus increases the conformability decreases and the ability of the film to perform comfortably as medical dressings decreases.

Figure 1A:
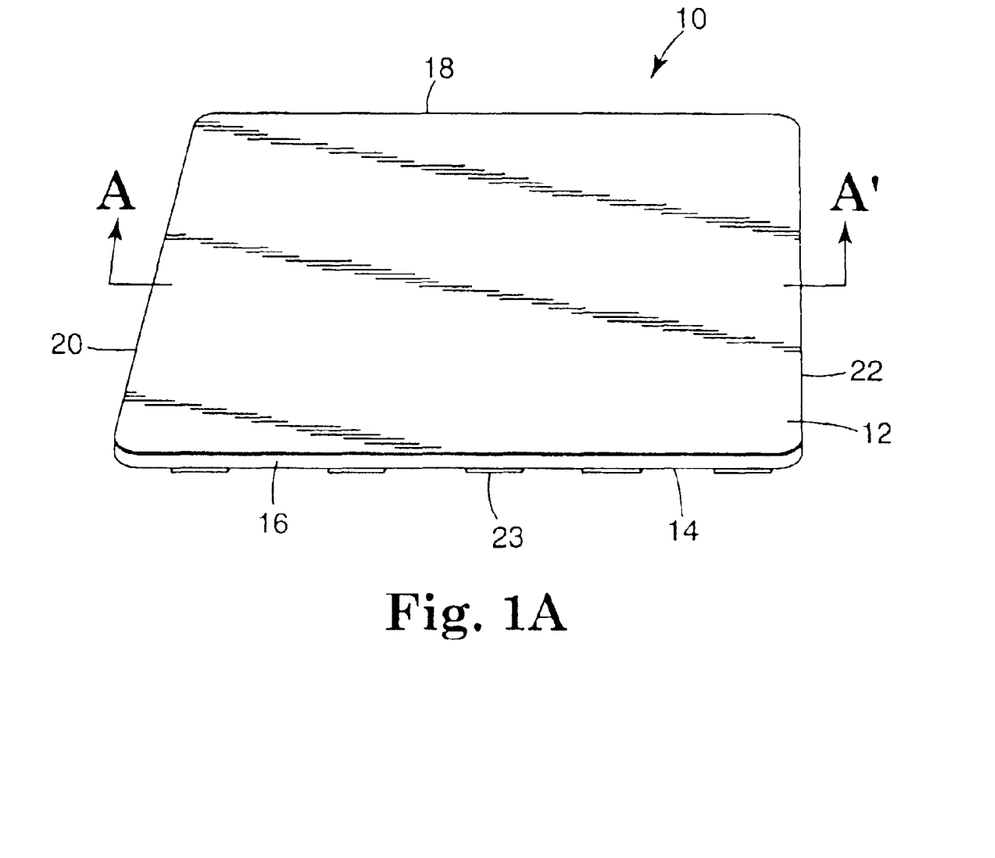
FIG. 1A is a perspective view of a medical dressing containing a breathable film constructed and arranged in accordance with the invention.

In reference now to the figures, an example breathable polymeric wound dressing 10 constructed in accordance with the invention is shown in perspective view in FIG. 1A. Wound dressing 10 includes a top surface 12, a bottom surface 14, first and second ends 16, 18, and edges 20, 22. Wound dressing 10 is constructed of a thin polymeric matrix that allows for release of moisture from bottom surface 14 to top surface 12. An adhesive 23 is positioned on the bottom surface 14, and also allows for release of moisture through the dressing 10.

In the implementation shown the adhesive is placed over only a portion of bottom surface 14, such as by the method taught in U.S. Pat. No. 4,798,201. In other implementations (shown later in FIGS. 2A–2D), the adhesive covers all or substantially all of bottom surface 14. When the adhesive covers substantially all of the bottom surface, then the adhesive itself should be breathable. However, when the adhesive covers significantly less than all of bottom surface 14, then the adhesive is optionally either breathable or not breathable.

Figure 1B:
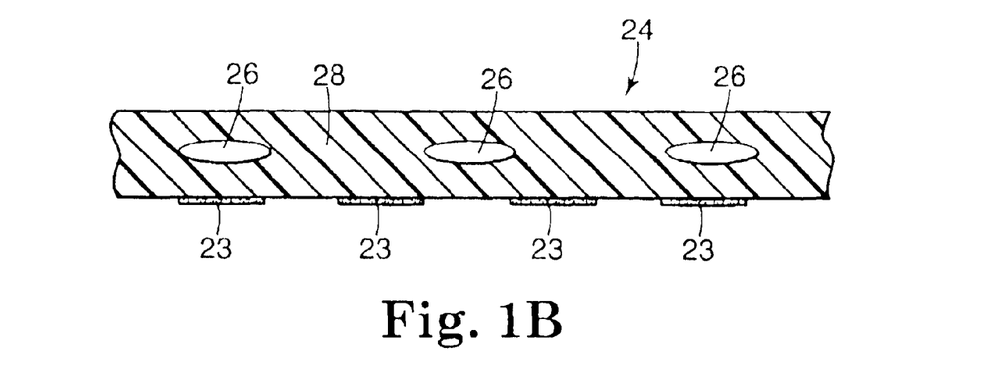
FIG. 1B is a fractional cross-sectional view of the medical dressing shown in FIG. 1A taken along plane A–A'.

A cross-sectional fragment 24 of wound dressing 10, taken along plane A–A', is depicted in FIG. 1B. Fragment 24 of dressing 10 includes a plurality of phases 26 positioned within matrix 28. In the embodiment shown, matrix 28 contains a single layer into which the plurality of phases 26 are positioned. Phases 26 can be formed within matrix 28 by, for example, coextruding the phases 26 and matrix 28 at the same time. In the embodiment depicted in FIGS. 1A and 1B, the phases are continuous between the ends 16 and 18 of the dressing 10, but are discontinuous from edge 20 to edge 22.

Figure 2A:
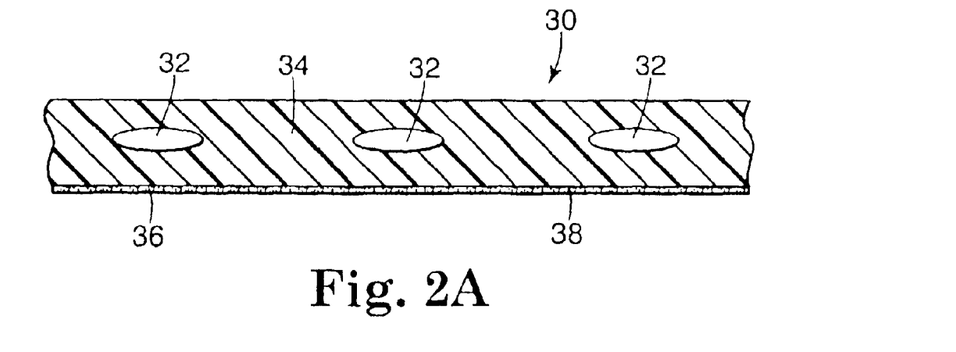
FIG. 2A is a fractional cross-sectional view of a conformable adhesive article constructed and arranged in accordance with the invention, showing a polymeric matrix surrounding a plurality of phases.
Figure 2B:
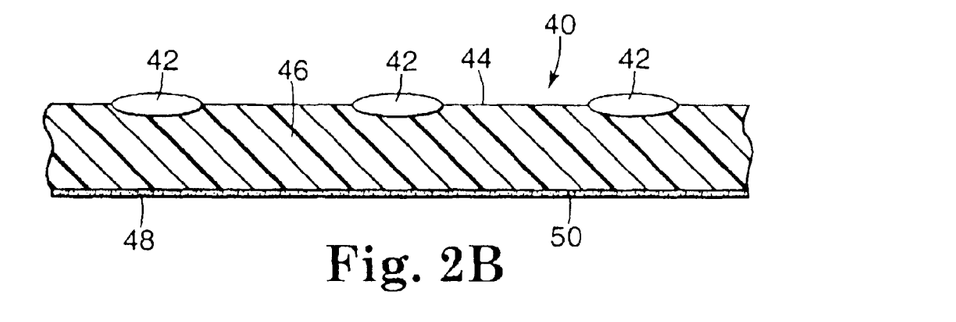
FIG. 2B is a fractional cross-sectional view of a conformable adhesive article constructed and arranged in accordance with the invention, showing a polymeric matrix with a plurality of phases adhered to a surface of the matrix.
Figure 2C:
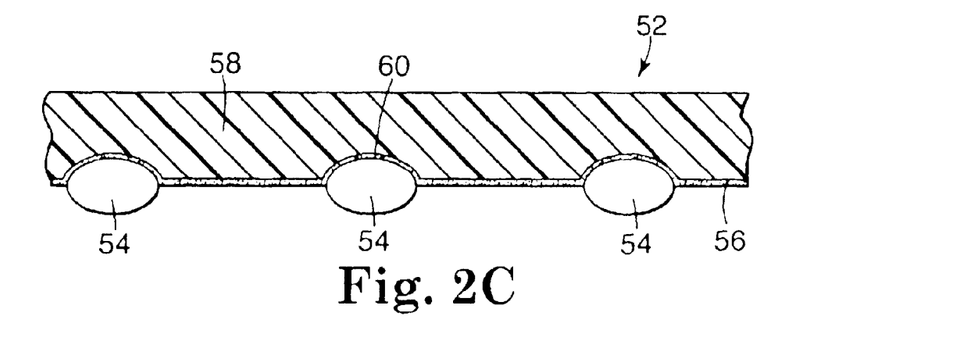
FIG. 2C is a fractional cross-sectional view of a conformable adhesive article constructed and arranged in accordance with the invention, showing an alternate implementation of a polymeric matrix with a plurality of phases adhered to a surface of the matrix.
Figure 2D:
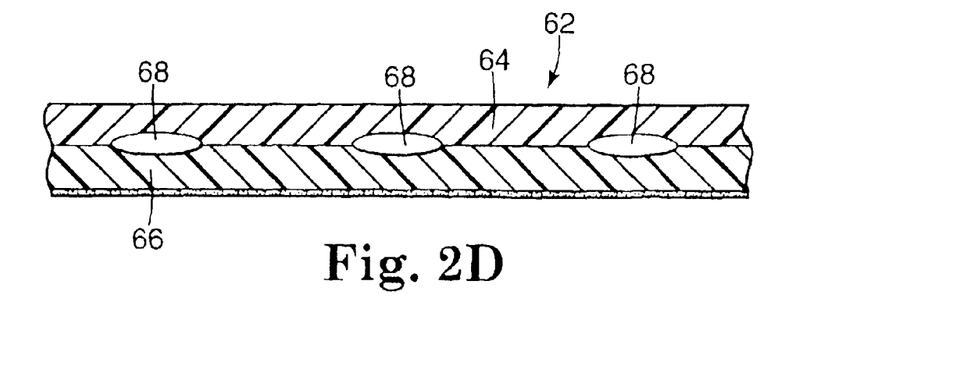
FIG. 2D is a fractional cross-sectional view of a conformable adhesive article constructed and arranged in accordance with the invention, showing a matrix having two layers.

FIGS. 2A through 2D show additional cross-sectional fragments of articles constructed in accordance with the invention. In FIG. 2A, fragment 30 includes a plurality of phases 32 entirely surrounded by matrix 34. An adhesive 36 is applied to the bottom surface 38 of fragment 30. In contrast, FIG. 2B shows fragment 40 with a plurality of phases 42 secured to an upper surface 44 of the matrix 46. An adhesive 48 is positioned on the bottom surface 50 of fragment 40. Yet another embodiment is shown in FIG. 2C, which depicts a fragment 52 with a plurality of phases 54 secured to the bottom surface 56 of the matrix 58 by adhesive 60. A further embodiment is shown in FIG. 2D, depicting fragment 62 with a matrix having an upper layer 64 and a lower layer 66. The phases 68 are positioned within the matrix between layers 64, 66.

In a specific implementation of the invention, the article includes an extruded breathable film and a plurality of distinct, co-extruded phases positioned proximate the film. The article is extruded as a continuous or substantially continuous web, with the phases discontinuous in a cross-web direction. The phases positioned proximate the film may be entirely within the film, partially within the film, or adhered to the exterior of the film. The extruded phases preferably have a width uniform to within a coefficient of variation of less than 8 percent for three consecutive discontinuous phases. The width of these extruded phases is measured in a cross-section of the film cut transverse (i.e., cross-web) to the machine direction (i.e., down-web) and is the largest dimension of the cross-section of the phases in the cross-web direction. In one embodiment, the phases are spaced at substantially uniform intervals in the cross-web direction.

The article can be made into a roll good that facilitates easy dispensing. The roll good includes a breathable polymeric matrix having a first surface and a second surface, a plurality of substantially continuous phases retained proximate the polymeric matrix, and an adhesive composition positioned on at least a portion of the first surface of the polymeric matrix. The roll good can include perforations to form individual lengths of sterile medical dressings.

The invention is further directed to processes for making a breathable polymeric co-extruded article. The phases can be co-extruded with the polymeric matrix, thereby forming a substantially integrated product with a strong interface between the matrix and the phases. Alternatively, incompatible materials can be co-extruded to form the article. In such implementations, the phases are preferably encapsulated within the matrix in order to secure the phases in place. Thus, the plurality of phases can be substantially surrounded by the polymeric matrix and have a strong interface with the matrix, or can be substantially surrounded by the polymeric matrix and not have a strong interface with the polymeric matrix.

Numerous alternative processes can be used for forming the articles of the invention. These processes can alter the properties of the finished product, as well as the structure of the product. For example, the plurality of phases can be retained on the same surface of the polymer matrix as the adhesive composition, or can be retained on an opposite surface. When the plurality of phases are retained on the same surface as the adhesive composition, the phases can be intermediate the adhesive composition and the surface of the polymeric matrix. The plurality of phases can be heat laminated between a polymeric matrix having at least two layers, extruded in two stages, solvent cast onto a release sheet, etc.

When the breathable polymeric article is made by co-extrusion in other implementations, two extruders provide molten streams of first and second extrudable materials. The extrudable materials are extruded from the die such that the first extrudable material substantially surrounds or forms a matrix around the second extrudable material, which becomes phases embedded within the matrix. Alternatively, a third extruder may be used to feed a third material into the die to form a matrix having a different material for each matrix layer.

A specific process suitable for forming the breathable article includes providing an extrudable material and an extrusion die, as described in U.S. patent application 09/365,286, entitled "Polymeric Articles Having Embedded Phases", filed Jul. 30, 1999. In a specific embodiment, the die contains two chambers and an adjustable vane between the chambers. The vane contains a cavity having at least one input orifice positioned to receive extrudable material and at least one exit orifice. The cavity is designed so that the difference in pressure of molten polymer from one end to the other is sufficiently small to yield embedded phases of good uniformity extruded from the exit orifices. A matrix material is extruded through the chambers of the die, and a phase material is extruded through the exit orifice in the vane to produce a co-extruded web containing the matrix and phase materials. The phase material is embedded between the two layers of the first material.

Figure 3A:
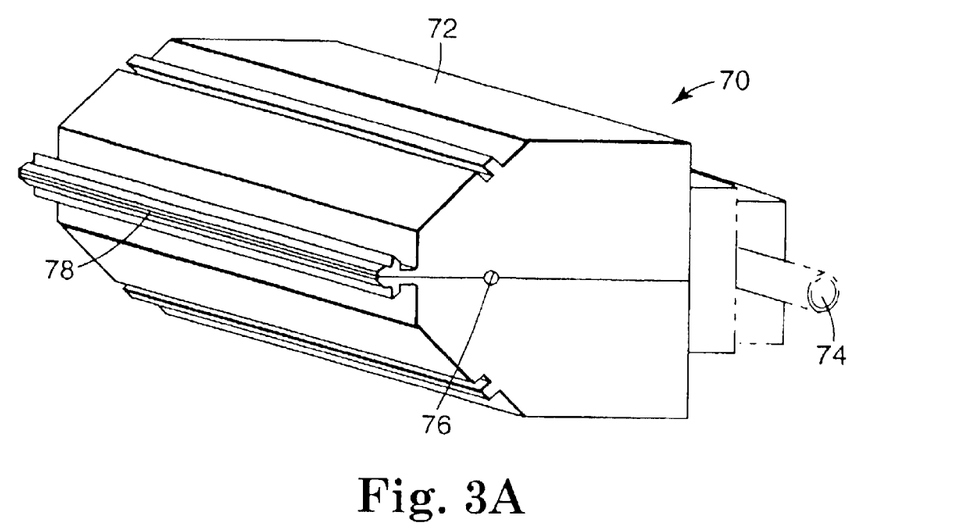
FIG. 3A is a perspective view of an extrusion die constructed in accordance with an embodiment of the invention.

In reference now to FIG. 3A, a perspective view of an extrusion die 70 is depicted showing an exemplary apparatus that can be used to form a breathable polymeric article in accordance with the invention. The die 70 depicted in FIG. 3A is one apparatus suitable for formation of the article of the invention, and other apparatuses are also appropriate for various implementations. Die 70 includes a body 72 that has at least first and second orifices 74 and 76. Orifice 74 provides entry for a first extrudable material, while orifice 76 provides entry for a second extrudable material. Extrusion die 70 also includes an exit port 78. The width of port 78 (also called the die gap) is typically 1000 μm or less. Extrudable materials enter die 70 at orifices 74 and 76, respectively, flow through die 70, and then leave die 70 at exit port 78 as a co-extruded web.

Figure 3B:
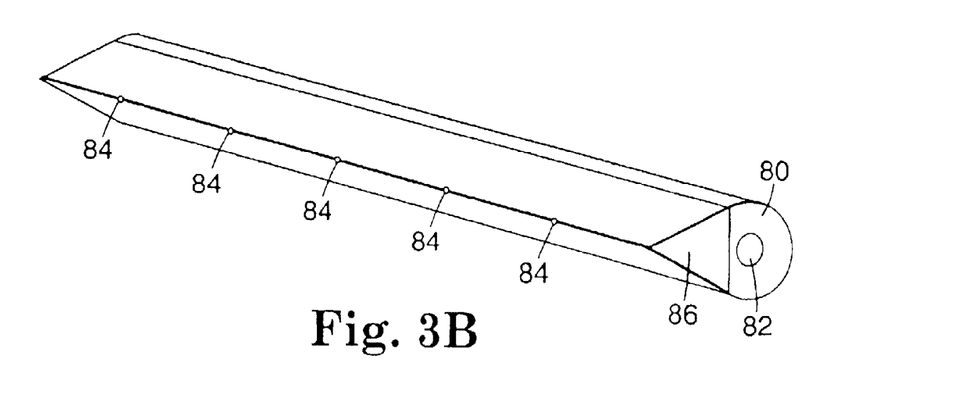
FIG. 3B is a perspective view of an extrusion die vane constructed in accordance with an embodiment of the invention.

Within extrusion die 70 is an adjustable vane 80, shown in FIG. 3B. Adjustable vane 80 includes at least two orifices 82 and 84. Entrance orifice or orifices 82 allow entry of polymeric material for the interior of vane 80, and outlet orifices 84 permit the exit of polymeric material from the interior of vane 80. The shape and position of outlet orifices 84 define the shape and position of the plurality of distinct embedded phases in the polymeric web. Advantageously, tip 86 of vane 80 may be removable and replaceable to allow placement of different tips having different configurations of orifices 84 to form different web configurations. Vane 80 is thus adjustable in at least one of two modes. The vane can be pivoted so the tip can be moved closer to the exit of one die chamber or the other causing a difference in die gap for the exits of each of the two matrix layers. This can result in a different matrix layer thickness if each layer is made with matrix material having a similar melt viscosity. Alternatively, different exit gaps can result in a similar matrix layer thickness if each layer is made with matrix material having a different melt viscosity. The vane can also be adjusted by replacement of tip 86 with one having orifices of different shapes and spacing.

This implementation is advantageous in that materials are co-extruded in a controlled manner. The materials are brought together in the melt state, thereby allowing for improved adhesion to one another. In addition, even when the materials are not compatible, they may still be co-extruded in order to produce a breathable polymeric article.

If one matrix material is less viscous than the other, it is possible to narrow the gap through which the less viscous matrix material flows in order to maintain uniformity of the thickness of each of the two matrix layers. The gap can be altered during processing in order to account for variations in processing conditions, such as changes in the temperature, pressure, flow rate, or viscosity over time. Thus, if die 70 has a warmer upper portion than lower portion resulting in lower viscosity of materials flowing through the upper gap, then the gap can be adjusted to account for this change in viscosity. In addition, the gap can be altered to achieve a different thickness in each matrix layer. This is particularly useful when each matrix layer is of a different material, e.g., a thermoplastic elastomer and a pressure-sensitive adhesive, where different properties are desired from each layer of the matrix.

The co-extrusion process of the invention is able to reproduce in the phases the relative dimensions of the orifices in the tip to a degree that has not previously been known. In one aspect, where the orifices have substantially the same dimensions, the width of the discontinuous embedded phases are relatively uniform. The coefficient of variation (COV) of the width of any three consecutive discontinuous phases is less than 8, preferably less than 5 and more preferably less than 3 percent when three or more similarly sized orifices are used.

Another way of modifying the properties of the webs of the invention is to use specific materials having desired properties for the layers of the matrix and the embedded phases. Suitable polymeric materials for forming the matrix layers and embedded phases of the inventive coextruded web include pressure sensitive adhesives, thermoplastic materials, elastomeric materials, polymer foams, high viscosity liquids, etc.

"Pressure-sensitive adhesives" (PSAs) include adhesives that display permanent and aggressive tackiness to a wide variety of substrates after applying only light pressure. PSAs have a four-fold balance of adhesion, cohesion, stretchiness, and elasticity, and are normally tacky at use temperatures, which is typically room temperature (i.e., about 20° C. to about 30° C.). PSAs also typically have an open time tack (i.e., period of time during which the adhesive is tacky at room temperature) on the order of days and often months or years. An accepted quantitative description of pressure-sensitive adhesives is given by the Dahlquist criterion line (as described in *Handbook of Pressure-Sensitive Adhesive Technology,* Second Edition, D. Satas, ed., Van Nostrand Reinhold, New York, N.Y., 1989, pages 171–176), which indicates that materials having a storage modulus (G') of less than about $3 \times 10^5$ Pascal (measured at 10 radians/second at a temperature of about 20° C. to about 22° C.) have pressure-sensitive adhesive properties, but materials having a G' in excess of this value do not.

"Nonpressure-sensitive adhesives" include nontacky polymeric materials as well as tacky polymeric materials that, when in the melt state, do not display pressure sensitive properties, or other materials that have adhesive properties at room temperature but do not meet the Dahlquist criterion as described above. Such materials have a storage modulus (G') of at least about $3 \times 10^5$ Pascal (measured at 10 radians/second at a room temperature of about 20° C. to about 22° C.). These materials can be nontacky thermoplastic materials, which can be elastomeric or non-elastomeric. Alternatively, they can be nontacky elastomers.

Preferred materials for use in preparing the articles of the present invention, whether they include pressure-sensitive adhesives or nonpressure-sensitive adhesives, are melt processable. That is, they are fluid or pumpable at the temperatures used to melt process the webs (e.g., about 50° C. to about 300° C.), and they form films. Furthermore, preferred materials do not significantly degrade or gel at the temperatures employed during melt processing (e.g., extruding or compounding). Preferably, such materials have a melt viscosity of about 10 poise to about 1,000,000 poise, as measured by capillary melt rheometry at the processing temperatures and shear rates employed in extrusion. Typically, suitable materials possess a melt viscosity within this range at a temperature of about 175° C. and a shear rate of about 100 seconds$^{-1}$.

Pressure-sensitive adhesives useful in articles of the present invention can be any material that has pressure-sensitive adhesive properties as described above at use temperatures, which are typically about room temperature (i.e., about 20° C. to about 30° C.). Generally, although not necessarily, particularly useful pressure-sensitive adhesives are amorphous with a glass transition temperature (Tg) of less than about 20° C.

The pressure-sensitive adhesive material can include a single pressure-sensitive adhesive, a mixture (e.g., blend) of several pressure-sensitive adhesives, or a mixture (e.g., blend) of a pressure-sensitive adhesive and a material that is a nonpressure-sensitive adhesive (e.g., a nontacky thermoplastic material, which may or may not be elastomeric), as long as the layer has pressure-sensitive adhesive properties. Examples of some pressure-sensitive adhesive blends are described in PCT Publication Nos. WO 97/23577, 97/23249, and 96/25469. Similarly, a suitable nonpressure-sensitive adhesive matrix layer can include a single material that is a nonpressure-sensitive adhesive, a mixture of several such materials, or a mixture of a material that is not a pressure-sensitive adhesive with a pressure-sensitive adhesive, as long as the layer does not have pressure-sensitive adhesive properties.

Pressure-sensitive adhesives useful in the present invention can be self-tacky or require the addition of a tackifier. Such materials include, but are not limited to, tackified natural rubbers, tackified synthetic rubbers, tackified styrene block copolymers, self-tacky or tackified acrylate or methacrylate copolymers, self-tacky or tackified poly-α-olefins, and self-tacky or tackified silicones. Examples of suitable pressure-sensitive adhesives are described in U.S. Pat. No. Re 24,906 (Ulrich), U.S. Pat. No. 4,833,179 (Young et al.), U.S. Pat. No. 5,209,971 (Babu et al.), U.S. Pat. No. 2,736,721 (Dexter), and U.S. Pat. No. 5,461,134 (Leir et al.), for example. Others are described in the *Encyclopedia of Polymer Science and Engineering,* vol. 13, Wiley-Interscience Publishers, New York, 1988, and the *Encyclopedia of Polymer Science and Technology,* vol. 1, Interscience Publishers, New York, 1964.

Useful natural rubber pressure-sensitive adhesives generally contain masticated natural rubber, one or more tackifying resins, and one or more antioxidants. Useful synthetic rubber adhesives are generally rubbery elastomers, which are either inherently tacky or nontacky and require tackifiers. Inherently tacky (i.e., self-tacky) synthetic rubber pressure-sensitive adhesives include for example, butyl rubber, a copolymer of isobutylene with less than 3 percent isoprene, polyisobutylene, homopolymers of isoprene, polybutadiene, or styrene/butadiene rubber.

Styrene block copolymer pressure-sensitive adhesives generally comprise elastomers of the A-B or A-B-A type, wherein, in this context, A represents a thermoplastic polystyrene block and B represents a rubbery block of polyisoprene, polybutadiene, or poly(ethylene/butylene), and tackifying resins. Examples of the various block copolymers useful in block copolymer pressure-sensitive adhesives include linear, radial, star, and tapered block copolymers. Specific examples include copolymers such as those available under the trade designations Kraton from Shell Chemical Co., Houston, Tex., and Europrene Sol from EniChem Elastomers Americas, Inc., Houston, Tex. Examples of tackifying resins for use with such styrene block copolymers include aliphatic olefin-derived resins, rosin esters, hydrogenated hydrocarbons, polyterpenes, terpene phenolic resins derived from petroleum or turpentine sources, polyaromatics, coumarone-indene resins, and other resins derived from coal tar or petroleum and having softening points above about 85° C.

(Meth)acrylate (i.e., acrylate and methacrylate or "acrylic") pressure-sensitive adhesives generally have a glass transition temperature of about −20° C. or less and typically include an alkyl ester component such as, for example, isooctyl acrylate, 2-ethyl-hexyl acrylate, and n-butyl acrylate, and a polar component such as, for example, acrylic acid, methacrylic acid, ethylene vinyl acetate, and N-vinyl pyrrolidone. Preferably, acrylic pressure-sensitive adhesives comprise about 80 wt-% to about 100 wt-% isooctyl acrylate and up to about 20 wt-% acrylic acid. The acrylic pressure-sensitive adhesives may be inherently tacky or tackified using a tackifier such as a rosin ester, an aliphatic resin, or a terpene resin.

Poly-α-olefin pressure-sensitive adhesives, also called poly(1-alkene) pressure-sensitive adhesives, generally comprise either a substantially uncrosslinked polymer or an uncrosslinked polymer that may have radiation activatable functional groups grafted thereon as described in U.S. Pat. No. 5,209,971 (Babu et al.). Useful poly-α-olefin polymers include, for example, $C_3$–$C_{18}$ poly(1-alkene) polymers. The poly-α-olefin polymer may be inherently tacky and/or include one or more tackifying materials such as resins derived by polymerization of $C_5$–$C_9$ unsaturated hydrocarbon monomers, polyterpenes, synthetic polyterpenes, and the like.

Silicone pressure-sensitive adhesives comprise two major components, a polymer or gum and a tackifying resin. The polymer is typically a high molecular weight polydimethylsiloxane or polydimethyldiphenylsiloxane that contains residual silanol functionality (SiOH) on the ends of the polymer chain, or a block copolymer comprising polydiorganosiloxane soft segments and urea terminated hard segments. The tackifying resin is generally a three-dimensional silicate structure that is endcapped with trimethylsiloxy groups (OSiMe$_3$) and also contains some residual silanol functionality. Silicone pressure-sensitive adhesives are described in U.S. Pat. No. 2,736,721 (Dexter). Silicone urea block copolymer pressure-sensitive adhesive are described in U.S. Pat. No. 5,461,134 (Leir et al.), and PCT Publication Nos. WO 96/34029 and 96/35458.

Nonpressure-sensitive adhesive polymeric materials used in the articles of the present invention include one or more thermoplastic materials, which may or may not be elastomeric materials, and elastomers. These may be adhesive (i.e., tacky) when in the melt state or nonadhesive (i.e., nontacky) materials, as long as the adhesive materials are not pressure sensitive, as defined above.

Thermoplastic materials are generally materials that flow when heated sufficiently above their glass transition temperature and become solid when cooled. They may be elastomeric or non-elastomeric. Thermoplastic materials useful in the present invention that are generally considered non-elastomeric include, for example, polyolefins such as isotactic polypropylene, low density polyethylene, linear low density polyethylene, very low density polyethylene, medium density polyethylene, high density polyethylene, polybutylene, non-elastomeric polyolefin copolymers or terpolymers such as ethylene/propylene copolymer and blends thereof; ethylene-vinyl acetate copolymers such as those available under the trade designation Elvax from E.I. DuPont de Nemours, Inc., Wilmington, Del.; ethylene acrylic acid copolymers; ethylene methacrylic acid copolymers such as those available under the trade designation Surlyn 1702 from E.I. DuPont de Nemours, Inc.; polymethylmethacrylate; polystyrene; ethylene vinyl alcohol; polyesters including amorphous polyester; polyamides; fluorinated thermoplastics such as polyvinylidene fluoride and fluorinated ethylene/propylene copolymers; halogenated thermoplastics such as chlorinated polyethylene; polyether-block-amides such as those available under the trade designation Pebax 5533 from Elf-Atochem North America, Inc. Philadelphia, Pa.

Thermoplastic materials that have elastomeric properties are typically called thermoplastic elastomeric materials. Thermoplastic elastomeric materials are generally defined as materials that exhibit high resilience and low creep as though they were covalently crosslinked at ambient temperatures, yet process like thermoplastic non-elastomers and flow when heated above their softening point. Thermoplastic elastomeric materials useful in the articles of the present invention include, for example, linear, radial, star, and tapered block copolymers such as those listed above with respect to pressure-sensitive adhesives (e.g., styrene-isoprene block copolymers, styrene-(ethylene-butylene) block copolymers, styrene-(ethylene-propylene) block copolymers, and styrene-butadiene block copolymers); polyetheresters such as that available under the trade designation Hytrel G3548 from E.I. DuPont de Nemours, Inc.; polyether block amides such as Pebax available from Atochem, Philadelphia, Pa.; ethylene copolymers such as ethylene vinyl acetates, ethylene/propylene copolymer elastomers or ethylene/propylene/diene terpolymer elastomers and metallocene polyolefins such as polyethylene, poly (1-hexene), copolymers of ethylene and 1-hexene, and poly (1-octene); thermoplastic elastomeric polyurethanes such as that available under the trade designation Morthane PE44-203 polyurethane from Morton International, Inc., Chicago, Ill. and the trade designation Estane 58237 polyurethane from B. F. Goodrich Company, Cleveland, Ohio; polyvinylethers; poly-α-olefin-based thermoplastic elastomeric materials such as those represented by the formula —(CH$_2$CHR)$_x$ where R is an alkyl group containing 2 to 10 carbon atoms, and poly-α-olefins based on metallocene catalysis such as Engage EG8200, ethylene/poly-α-olefin copolymer available from Dow Plastics Co., Midland, Mich.

Elastomers, as used herein, are distinct from thermoplastic elastomeric materials in that the elastomers require crosslinking via chemical reaction or irradiation to provide a crosslinked network, which imparts modulus, tensile strength, and elastic recovery. Elastomers useful in the present invention include, for example, natural rubbers such as CV-60, a controlled viscosity grade of rubber, and SMR-5, a ribbed smoked sheet rubber; butyl rubbers, such as Exxon Butyl 268 available from Exxon Chemical Co., Houston, Tex.; synthetic polyisoprenes such as Cariflex, available from Shell Oil Co., Houston, Tex., and Natsyn 2210, available from Goodyear Tire and Rubber Co., Akron, Ohio; ethylene-propylenes; polybutadienes; polybutylenes; polyisobutylenes such as Vistanex MM L-80, available from Exxon Chemical Co.; and styrene-butadiene random copolymer rubbers such as Ameripol Synpol 1011A, available from American Synpol Co., Port Neches, Tex.

Foams are those materials made by combining the above polymeric materials with blowing agents. The resulting mixtures are then subjected to various changes known in the art to activate the blowing agent used to form a multiplicity of cells within the polymer. Additional crosslinking may occur to cause resulting foams to be more stable. A particularly useful foam, when an elastic foam matrix is desired, is that disclosed in Ser. No. 09/325,963, "Breathable Polymer Foams" filed Jun. 4, 1999 and incorporated herein by reference. High viscosity liquids are any that do not diffuse through the matrix material and prematurely escape the article of the invention. These include, for example, various silicone oils, mineral oils and specialty materials having a sharp melting temperatures below room temperature.

Viscosity reducing polymers and plasticizers can also be blended with the elastomers. These viscosity reducing polymers include thermoplastic synthetic resins such as polystyrene, low molecular weight polyethylene and polypropylene polymers and copolymers, or tackifying resins such as Wingtack™ resin from Goodyear Tire & Rubber Company, Akron, Ohio. Examples of tackifiers include aliphatic or aromatic liquid tackifiers, aliphatic hydrocarbon resins, polyterpene resin tackifiers, and hydrogenated tackifying resins. Additives such as-dyes, pigments, antioxidants, antistatic agents, bonding aids, antiblocking agents, slip agents, heat stabilizers, photostabilizers, foaming agents, glass bubbles, starch and metal salts for degradability or microfibers can also be used in the elastomeric phase. Suitable antistatic aids include ethoxylated amines or quaternary amines such as those described, for example, in U.S. Pat. No. 4,386,125 (Shiraki), which also describes suitable antiblocking agents, slip agents and lubricants. Softening agents, tackifiers or lubricants are described, for example, in U.S. Pat. No. 4,813,947 (Korpman) and include coumarone-indene resins, terpene resins, hydrocarbon resins and the like. These agents can also function as viscosity reducing aids. Conventional heat stabilizers include organic phosphates, trihydroxy butyrophenone or zinc salts of alkyl dithiocarbonate.

Various additives may be incorporated into the phase(s) and/or the matrix to modify the properties of the finished article. For example, additives may be incorporated to improve the adhesion of the phases and the matrix to one another. The article may also be laminated to a fibrous web. Preferably, the fibrous web is a nonwoven web such as a consolidated or bonded carded web, a meltblown web, a spunbond web, or the like. The fibrous web alternatively is bonded or laminated to the matrix by adhesives, thermal bonding, extrusion, ultrasonic welding or the like. Preferably, a co-extruded web can be directly extruded onto one or more fibrous webs.

Short fibers or microfibers can be used to reinforce the distinct phases or matrix layers for certain applications. These fibers include polymeric fibers, mineral wool, glass fibers, carbon fibers, silicate fibers and the like. Further, certain particles can be used, including carbon and pigments. Glass bubbles or foaming agents may be used to lower the density of the matrix layer or embedded phases and can be used to reduce cost by decreasing the content of an expensive material or the overall weight of a specific article. Suitable glass bubbles are described in U.S. Pat. Nos. 4,767,726 and 3,365,315. Blowing agents used to generate foams in melt processable materials are known in the art and include azodicarbonamides such as SAFOAM RIC-50 sodium bicarbonate-based chemical blowing agent. Fillers can also be used to some extent to reduce costs. Fillers, which can also function as antiblocking agents, include titanium dioxide and calcium carbonate.

A number of additional steps can optionally be performed. For example, the article may be uniaxially or biaxially oriented, either sequentially or simultaneously, can be cured (such as through heat, electromagnetic radiation, etc.), can be embossed, laminated, or can be dusted with various tack-reducing agents.

Articles of the invention are suitable for use in various medical articles, such as wound dressings and tapes, surgical drapes, and wound closure systems. In certain embodiments, distinct phases are formed in the polymeric matrix in order to provide increased strength and improved handling without affecting the overall conformability, transparency or breathability of the polymeric material. Preferred matrix materials for use in constructing such medical articles include breathable polymers such as polyurethanes, polyesters (e.g., Hytrel™ 4056 resin from Dupont, Wilmington, Del.), and polyether block amides (e.g., made from Pebax™ 3533, Pebax™ MX-1657, and Pebax ™ MX-1074, all available from Elf Atochem, Philadelphia, Pa.). Also preferred are polyolefins, e.g., polyethylene and polypropylene, when constructed in a manner to allow breathability, such as when co-extruded with oil to form a porous film. Combinations of these two types of preferred matrix materials could also be used. Preferred phase materials for use in constructing such medical articles include polyamides, polyethylene, polypropylene, polyesters and styrene block copolymers, such as Kraton™ block copolymers.

In one preferred embodiment, distinct phases of polyester (e.g., Eastar™ 6763 from Eastman Chemical Company, Kingsport, Tenn.) are formed in a breathable polyurethane web matrix (e.g., Estane™ 58237 from B. F. Goodrich Company, Cleveland, Ohio) to increase strength and aid in the ability to handle and position the article in final sheet or tape form. This represents a significant improvement over current surgical dressings formed of polyurethane that are difficult to handle because they are too flexible and thus do not easily maintain a shape. The addition of phases to the polyurethane matrix allows for retention of breathability (at least about 300 grams/square meter/24 hours, and preferably at least about 600 grams/square meter/24 hours by Moisture Vapor Transmission Rate–Upright Method) while increasing tensile strength and web handling characteristics. The down-web tensile strength of the resulting webs typically is increased at least 50 percent over comparable webs not having discontinuous phases and preferably is increased at least 100 percent.

Alternate methods of making the above breathable article are lamination and other extrusion methods. One method of making the article by lamination involves placing a plurality of synthetic or natural fibers in a parallel direction between two sheets of breathable elastic material. The resulting sandwich can be pressed together under heat by means of a platten press of a hot nip. An alternate extrusion method is that disclosed in Krueger et al, U.S. Pat. No. 5,429,856, except the two matrix layers are of an elastic breathable material and the discontinuous phases include preferably inelastic thermoplastic materials.

The precise extruders employed in the inventive process are not critical as any device able to convey melt streams to a die of the invention is satisfactory. However, it is understood that the design of the extruder screw will influence the capacity of the extruder to provide good polymer melt quality, temperature uniformity, and throughput. A number of useful extruders are known and include single and twin screw extruders. These extruders are available from a variety of vendors including Davis-Standard Extruders, Inc. (Pawcatuck, Conn.), Black Clawson Co. (Fulton, N.Y.), Berstorff Corp (North Carolina), Farrel Corp. (Connecticut), Moriyama Mfg. Works, Ltd. (Osaka, Japan). Other apparatus capable of pumping organic melts may be employed instead of extruders to deliver the molten strearns to the forming die of the invention. They include drum unloaders, bulk melters and gear pumps. These are available from a variety of vendors, including Graco LTI (Monterey, Calif.), Nordson (Westlake, Calif.), Industrial Machine Manufacturing (Richmond, Va.), Zenith Pumps Div., Parker Hannifin Corp., (North Carolina).

Once the molten streams have exited the pump, they are typically transported to the die through transfer tubing and/or hoses. It is preferable to minimize the residence time in the tubing to avoid problems of, for example, melt temperature variation. This can be accomplished by a variety of techniques, including minimizing the length of the tubing, providing appropriate temperature control of the tubing, and utilizing static mixers in the tubing to maintain a homogeneous temperature in the tubing. Patterned tools which contact the web can provide surface texture or structure to improve the ability to tear the web in the cross web or transverse direction without affecting the overall tensile strength or other physical properties of the product.

EXAMPLES

The invention is further illustrated by the following examples, which are not intended to limit the scope of the invention. In the examples, all parts, ratios and percentages are by weight unless otherwise indicated. The following test methods were used to characterize the articles in the following examples:

Test Methods

Tensile Strength and Elongation

Tensile strength and elongation in the down-web direction of co-extruded articles were determined in the following manner. A 10.2 cm long by 2.5 cm wide sample was placed between the jaws of an Instron™ Tensile Tester to expose a 5.1 cm gauge length. The crosshead and chart speeds were set at 25.4 cm/min. The jaws were drawn apart at 25.4 cm/min until the machine detected a break. Tensile strength and percent elongation were calculated by the Instron™ software. Tensile strength measurements (each with 3 replications) were taken on samples oriented in the cross web direction (with force of pull perpendicular to the orientation of the phases) and in the machine direction (with machine force of pull parallel to the orientation of the phases).

Moisture Vapor Transmission Rate (MVTR)

Moisture vapor transmission rates of the samples were tested using either the upright method (A) or inverted method (B) as described below.

A—Upright Method: Glass bottles were filled with approximately 50 ml of water. Three test samples and three control samples were cut into 3.8 cm diameter samples using a round die cutter. The samples were placed between two foil rings that had holes cut in the centers. A rubber gasket was placed between the bottom of the foil and the glass container. A screw cap with a 3.8 cm diameter hole was attached to the glass jar enclosing the foil-sample sandwich and gasket to the glass. The samples were conditioned for four hours at 40° C. at 20% relative humidity in a control chamber. The cap was then tightly secured to the jar and the jar was removed from the chamber and weighed on an analytical balance to the nearest 0.01 gram. The jars were returned to the chamber for at least 18 hrs. (at the conditions listed above). The bottles were then removed and weighed immediately to the nearest 0.01 gram. Moisture vapor rates were calculated by the change in weight multiplied by the exposed area divided by the time they were exposed. Rates are reported in grams per square meter in 24 hours.

B—Inverted Method: The same procedure was followed as outlined above. However, after the samples were conditioned and weighed, they were returned to the chamber and the bottles were inverted so that the water contacted the test surface. The bottles were left undisturbed for at least 18 hrs. The bottles were then removed and weighed, and the moisture vapor transmission rate was calculated as above.

Conformability (Hand)

The total Hand conformability in grams of example sheet materials or tapes provides a measure of the drape/conformability of these materials. Those materials with a relatively high Hand value are stiff and nonconformable. Conversely, relatively low Hand values reflect soft, conformable materials. The Hand values reported for the following examples were obtained on a Thwing-Albert Handle-O-Meter Model No. 211-300 (Thwing-Albert Instrument Co., Philadelphia, Pa.), according to the procedures outlined in the instruction manual included with Model No. 211-300. All of the Hand measurements were performed on about 10 cm square sheet materials that were powdered with talc to reduce friction. Hand measurements (each with 3 replications) were taken on samples oriented in the cross-web direction (with machine bar parallel to the orientation of the phases) and in the machine direction (with machine bar perpendicular to the orientation of the distinct phases).

Conformability (Modulus)

$F_{10}$ modulus as referred to herein is a measure of the force to elongate a sample 10 percent and is effectively determined using an Instron Unit Model 1102 from Instron Corp., 2500 Washington Street, Canton, Mass. The cross-head speed of the Instron was set at ten inches per minute and the chart speed is set at ten inches (25.4 cm) per minute. The gauge length is set at two inches (5 cm) with the test sample cut to test a one-inch width (2.54 cm).

Modulus measurements (each with 3 replications) were taken on samples oriented in the cross-web direction (with machine bar parallel to the orientation of the phases) and in the machine direction (with machine bar perpendicular to the orientation of the distinct phases).

Examples 1 and 2

Examples 1 and 2 describe the preparation of extruded articles having an elastic continuous polyurethane matrix and a plurality of distinct inelastic phases. The inelastic phases comprised either modified polyester (Example 1) or polyethylene (Example 2).

For Example 1, a continuous extrusion was carried out using a 45 cm (18 in) wide Cloeren™ two-layer multi-manifold die (available as Model 96-1502 from Cloeren Co., Orange, Tex.) that had been modified as described in U.S. patent application 09/365,286, filed on Jul. 30, 1999. A vane tip containing 95 orifices was mounted to the vane manifold with socket head bolts. The vane tip had circular orifices each having a diameter of 508 microns (20 mils) and separated by a space of 4.1 mm (0.160 in) and extended from the vane tip 2.5 mm (0.100 in) into the matrix flow.

The continuous matrix material was an elastic material, Estane™ 58237 polyurethane (B.F. Goodrich, Cleveland, Ohio). It was fed with a 51 mm (2.0-inch) Berlyn™ single screw extruder that was operated at a temperature profile of zone 1—149° C. (300° F.), zone 2—171° C. (340° F.) and zones 3 to 7—204° C. (400° F.). The 51 mm extruder was run at 25 rpm with a head pressure of 31.1 MPa (4500 psi) to feed continuous matrix material. The discontinuous phase material was an inelastic thermoplastic polymer, Eastar™ 6763 glycol modified polyester (Eastman Chemical Co., Kingsport, Tenn.). It was fed with a 32 mm (1.25-inch)-Killion™ single screw extruder (available from Davis-Standard Killion Systems, Cedar Grove, N.J.) that was operated with a temperature profile of zone 1—188° C. (370° F.), zone 2—227° C. (440° F.) and zones 3 and 4—243° C. (470° F.). The 32 mm extruder was run at 6 rpm with a head pressure of 15.9 MPa (2300 psi) to feed discontinuous phase material through the modified vane in the die. The die was operated at 218° C. (425° F.). The extrudate comprising a two-layer polymer matrix containing embedded discontinuous phases running down-web was extruded into a nip formed by a chrome casting wheel, at 7.2° C. (45° F.) and a silicone coated nip roll, at 7.2° C. (45° F.). The web take-away speed was 11.3 m/min (37 fpm) resulting in an overall thickness of 43 microns (1.7 mils). The cast web was not oriented.

Example 2 was made as Example 1 except the discontinuous phase material was different and some conditions were changed. The temperature profile for the extruder that fed the continuous matrix material was zone 1—149° C. (300° F.), zone 2—166° C. (330° F.) and zones 3 to 7—199° C. (390° F.). The 51 mm extruder was run at 10 rpm with a head pressure of 13.8 MPa (2000 psi) to feed continuous matrix material. The discontinuous phase material was an inelastic thermoplastic polymer, Dowlex™ 10462N polyethylene. The temperature profile of the extruder that fed this material was zone 1— 182° C. (360° F.), zone 2—241° C. (465° F.) and zones 3 and 4—249° C. (480° F.). The 32 mm extruder was operated at 12 rpm with a head pressure of 3.5 MPa (500 psi) to feed discontinuous phase material. The temperature of the nip rolls was approximately 16° C. (60° F.). The material take-away speed was 5.2 m/min (17 fpm) resulting in an overall thickness of 79 microns (3.1 mils).

Example 3

Example 3 describes the preparation of an extruded adhesive article having two layers of different materials (polyacrylate PSA and polyurethane) that comprise an elastic continuous polymeric matrix and a plurality of distinct inelastic phases comprised of modified polyester.

An acrylic PSA (96 weight percent isooctyl acrylate/4 weight percent methacrylic acid, water suspension polymerized), prepared according to U.S. Pat. No. 4,833,179 (Young) was dried to about 90 weight percent and melt blended with Floral™ 85 (a tackifying resin available from Hercules Inc., Wilmington, Del.) in a weight ratio of acrylate to Foral™ of 80:20. The PSA was designated as PSA A.

Example 3 was made in a manner similar to Example 1 except that the two layers of continuous matrix material were made of different materials and an additional extruder was used. The first layer of continuous matrix material was made of a tacky elastomeric material, PSA A, and the second layer was made of the elastic thermoplastic polymer, Estane™ 58237 polyurethane. The first continuous matrix material was fed with a first extruder, a 34 mm fully intermeshing, co-rotating Leistritz™ twin screw extruder that used an increasing temperature profile reaching a peak temperature of 193° C. (380° F.). The 34 mm extruder was run at 180 rpm with gear pump speed of 4.7 rpm and a head pressure of 4.2 MPa (610 psi) to feed continuous matrix material into the first feed orifice of the die. The second material was fed with the 51 mm extruder into the second feed orifice of the die.

The resulting construction, which comprised an article having a PSA on one side, a polyurethane on the opposite side, and a distinct phase of polyester embedded strands, provides an example of a polymeric matrix composed of two different materials.

Example 4

Example 4 describes the preparation of a laminated adhesive article comprising a first layer of extruded elastic polyurethane film, a plurality of nylon monofilaments, a second layer of extruded elastic polyurethane film, and a polyacrylate PSA layer.

Twenty-five grams per square meter of a pressure sensitive adhesive prepared in accordance with U.S. Pat. No. Re. 24,906, comprising a copolymer of 96% units of isooctyl acrylate and 4% units acrylamide was applied to a 80 pound (36 kg) bleached release liner, one side coated, silicone paper (1-80BKG-157) (DCP-Loyha, Willowbrook, Ill.) using a standard horizontal knife coater.

A 0.6 mil (14 micron) film of ESTANE 58309 polyurethane resin (B. F. Goodrich, Cleveland, Ohio) was extruded using conventional methods. A silicone liner was placed on the bed of a fixture with a first layer of film. A 4 pound (1.8 kg) test Nylon Monofilament fishing line (Berkley & Co. Inc., Spirit Lake, Iowa) was threaded in a parallel manner over the first layer of film (2 mm apart) using the ends of the fixture and a second layer of film was place over the monofilaments with a second release liner placed over the sandwich laminate. The laminate was then placed in a heated press at 190° C. and 2 tons (1800 kg) of pressure. The laminate was then laminated to the adhesive surface to form an adhesive article of the present invention.

Example 5

Example 5 describes the preparation of an extruded article (from Example 1) coated with a microsphere-containing polyacrylate PSA.

A pressure sensitive adhesive matrix blended with polymeric microspheres was prepared and coated on one surface of the Example 1 extruded article according to the procedure described in Example 1 of Heinecke et al., U.S. Pat. No. 5,849,325 to provide an adhesive article of the present invention.

Example 6

Example 6 describes the preparation of an extruded article (from Example 1) pattern coated with a polyacrylate PSA.

The polyacrylate PSA described in Example 4 was pattern coated on one surface of the Example 1 extruded article to form a 25 percent void area grid according to the procedure described by Rawlings in U.S. Pat. No. 4,798,201.

Example 7

Example 7 describes the preparation of an extruded article having an elastic continuous polyurethane matrix and a plurality of distinct elastic phases comprised of ultra low density polyethylene.

The continuous extrusion was carried out using a 45 cm wide Cloeren™ three-layer multi-manifold die that had been modified as described in U.S. Pat. No. 5,429,856 (Krueger). A "comb" insert was bolted to the internal surface of one of the two unmodified vanes and snugly engaged with the second vane to allow the vanes to rotate in unison. The "comb" insert had orifices of 1.6 mm in length and a separation distance of 3.2 mm.

The continuous matrix material was an elastic material, Estane™ 58309 polyurethane. The matrix material was fed with a 63.5 mm Davis Standard™ single screw (available from Davis-Standard Corp., Pawcatuck, Conn.) that operated at a temperature profile of zone 1—149° C. (300° F.), zone 2—149° C. (300° F.), zone 3—177° C. (350° F.), zone 4—182° C. (360° F.), zone 5–6—188° C. (370° F.). The 63.5 mm extruder was run at 12 rpm to feed the continuous matrix material. The discontinuous phase material was an elastic thermoplastic polymer, Engage™ 8200 (ultra low density polyethylene, Dupont, Wilmongton, Del.). It was fed with 19 mm Killion™ single screw extruder (available from Davis-Standard Killion Systems, Cedar Grove, N.J.) that was operated with a temperature profile of zone 1—155° C. (311° F.), zone 2—180° C. (356° F.), zones 3–4—200° C. (392° F.), and zone 5—210° C. (410° F.). The 19 mm extruder was run at 87.5 rpm to feed the discontinuous phase material through the modified vane and cutouts in the die. The die was operated at 204° C. (400° F.). The extrudate comprising a two-layer polymer matrix containing embedded discontinuous phases running down-web was extruded into a nip formed by a chrome casting wheel and a silicone coated nip roll. The material take-away speed was 15.2 m/min (50 fpm) resulting in an overall basis weight of 3.0 g/cm².

Example 8

Example 8 describes the preparation of a laminated adhesive article comprising a layer of polyacrylate PSA, a layer of extruded elastic polyether block amide matrix and a plurality of distinct elastic phases comprised of polyether block amide blended with linear low density polyethylene and a white pigment.

A 13 micron (0.5 mil) film of Pebax 3533 polyether block amide resin (Elf Atochem, Philadelphia, Pa.) was extruded using a 19 mm Rheocord™ System 40 single screw extruded (Haake Buechler, Saddle Brook, N.J.) that was equipped with an Ultraflex 40 flex lip die (Extrusion Die Inc., Chippewa Falls, Wis.). The extruder was operated with a temperature profile of zone 1—177° C. (350° F.), zone 2—182° C. (360° F.), zone 3—193° C. (380° F.), and a die temperature of 204° C. (400° F.). The extruder was run at 35 rpm. The extruded film was laminated to a layer of the polyacrylate PSA (on silicone release liner) described in Example 4 using conventional laboratory lamination conditions.

The Ultraflex™ 40 die used above was then shimmed with 10 mil brass shim stock cut into 10 mm lengths to form a series of 5 apertures spaced 15 mm apart. A blended thermoplastic polymer was prepared by combining 50% Pebax™ 3533 and 50% LLDPE 7047 (Union Carbide), and then adding 3% white pigment concentrate CBE 101 E White (Charles B. Edwards & Co., Inc.). The blended polymer was fed into the shimmed Ultraflex 40 die using the 19 mm Rheocord System 40 extruder described above that was operated with a temperature profile of zone 1—177° C. (350° F.), zone 2— 188° C. (370° F.), and zones 3–4—199° C. (390° F.). The extruder was run at 10 rpm. The extruded discontinuous phase material was laminated to the Pebax™ film layer of the above laminate using the same conventional laboratory lamination conditions.

Example 9

Example 9 describes the preparation of an adhesive article having an extruded elastic continuous matrix comprised of porous polypropylene and a plurality of distinct inelastic polypropylene phases, and a layer of polyacrylate PSA.

Example 9 was made in a manner similar to Example 1 except the continuous matrix material was made of a melt blend of 40% by weight mineral oil and 60% by weight thermoplastic polymer, a dry blend of 95% SD45 polypropylene (Union Carbide, Danbury, Conn.) and 5% of a 2% Millad 3905 (Milliken Chemical, Inman, S.C.) nucleating agent concentrate. The Millad 3905 amounted to 0.1% of the total continuous matrix. The continuous matrix material was fed with a 34 mm fully intermeshing, co-rotating Leistritz™ twin screw extruder that used an increasing temperature profile reaching a peak temperature of 232° C. (450° F.). The discontinuous phase material was an inelastic thermoplastic polymer, PP 3374 polypropylene (Fina Oil & Chemical Co., Dallas, Tex.). A 32 mm (1.25-inch) Killion™ single screw extruder was operated with a temperature profile of zone 1—182° C. (360° F.), zone 2—221° C. (430° F.), and zones 3 and 4—243° C. (470° F.). The 32 mm extruder was run at 20 rpm with a head pressure of 15.9 mPa (2300 psi). The construction was then length oriented and tentered by a factor of 2.0 in both directions to provide porosity. The oriented temperature was 65° C. A detailed description of preparing porous films can be found in Shipman, U.S. Pat. No. 4,536,256.

The extruded film was laminated to a layer of polyacrylate PSA (on a silicone release liner) described in Example 4 using conventional laboratory lamination conditions.

Evaluations

Samples of articles from Examples 1, 3 and 9 were evaluated for stiffness (Hand and $F_{10}$ modulus measurements), tensile strength at break, percent elongation at break, and MVTR (upright method). The results are provided in Table 1 and are compared with comparative data from the commercial adhesive dressings TEGADERM™ HP (3M Company) and OP-SITE™ IV (Smith & Nephew)

TABLE 1

|  | Modulus (Hand) | | Modulus ($F_{10}$) (N/cm) | | Tension at Break (N/cm) | | Elongation at Break (%) | | MVTR gm/m²/24 hr Upright Method |
| --- | --- | --- | --- | --- | --- | --- | --- | --- | --- |
|  | MD | CD | MD | CD | MD | CD | MD | CD |  |
| Example 1 | 5 | 4 | 3.06 | 2.31 | 17.5 | 12.25 | 480 | 408 | 8900 |
| Example 3 | 7 | 4 | 3.12 | 2.19 | 26.25 | 11.38 | 640 | 380 | 500 |
| Example 9 | 18 | 6 | 5.6 | 4.03 | 13.1 | 8.93 | 92 | 91 | NA |
| TEGADERM HP[1] | 2 | 2 | 0.46 | 0.46 | 4.73 | 4.38 | 360 | 340 | 4000 |
| OP-SITE IU[2] | 1 | 1 | 0.72 | 0.72 | 9.98 | 9.45 | 545 | 555 | 1540 |

[1]TAGADERM ™ HP #9536HP, transparent dressing with label; 10 × 12 cm; Lot #2001-07 HD
[2]OP-SITE ™ IV3000 moisture responsive cannula dressing; 10 × 14 cm; Lot #9243

As seen from Table 1, the presence of distinct phases in Example 3 provided an adhesive article with significantly increased stiffness (higher Hand and $F_{10}$ Modulus values), significantly increased tensile strength and a high degree of breathability (MVTR greater than 300 gm/m²/24hr) as compared to the two commercial adhesive dressings that do not contain phases.

All patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

We claim:

1. A conformable adhesive article for use as a sterile medical dressing, the article comprising:

a substantially continuous breathable polymeric matrix comprising an elastic material, and having a first surface and a second surface;

a plurality of phases comprising an elastomeric material retained proximate the polymeric matrix, the plurality of phases substantially discontinuous in a first direction and substantially continuous in a second direction; and an adhesive composition positioned on at least a portion of the first surface of the polymeric matrix.

2. The conformable adhesive article according to claim 1, wherein the article has a Hand conformability of between approximately 2 and 10 in the first direction.

3. The conformable adhesive article according to claim 1, wherein the article has a Hand conformability of greater than 5 in the first direction.

4. The conformable adhesive article according to claim 1, wherein the article has a Hand conformability of between approximately 2 and 25 in the second direction.

5. The conformable adhesive article according to claim 1, wherein the article has a Hand conformability of greater than 10 in the second direction.

6. The conformable adhesive article according to claim 1, wherein the article has an inverted moisture vapor transmission rate of at least about 300 g/m²/24 hours.

7. The conformable adhesive article according to claim 1, wherein the article has an inverted moisture vapor transmission rate of at least about 1,500 g/m²/24 hours.

8. The conformable adhesive article according to claim 1, wherein the article has an inverted moisture vapor transmission rate of at least about 4,000 g/m²/24 hrs.

9. The conformable adhesive article according to claim 1, wherein the article has an upright moisture vapor transmission rate of at least about 300 g/m²/24 hrs.

10. The conformable adhesive article according to claim 1, wherein the article has an upright moisture vapor transmission rate of at least about 600 g/m²/24 hrs.

11. The conformable adhesive article according to claim 1, wherein the article has an upright moisture vapor transmission rate of at least about 1,000 g/m²/24 hrs.

12. The conformable adhesive article according to claim 1, wherein the plurality of phases retained proximate the polymeric matrix are substantially surrounded by the polymeric matrix.

13. The conformable adhesive article according to claim 12, wherein the plurality of phases substantially surrounded by the polymeric matrix are incompatible with the polymeric matrix.

14. The conformable adhesive article according to claim 1, wherein the breathable polymeric matrix is comprised of a material selected from the group consisting of polyurethanes, polyesters, and polyether block amides.

15. The conformable adhesive article according to claim 1, wherein the breathable polymeric matrix is comprised of a polyurethane.

16. The conformable adhesive article according to claim 1, wherein the breathable polymeric matrix and the plurality of phases are produced by coextrusion.

17. The conformable adhesive article according to claim 1, wherein the polymeric matrix material is solvent cast onto a release sheet.

18. The conformable adhesive article according to claim 1, wherein the article comprises a roll good.

19. The conformable adhesive article according to claim 18, wherein the roll good is perforated to form individual lengths of sterile medical dressings.

20. A conformable adhesive article for use as a sterile medical dressing, the article comprising: a substantially continuous breathable polymeric matrix comprising an elastic material, and having a first surface and a second surface, a plurality of phases retained proximate the polymeric matrix, the plurality of phases substantially discontinuous in a first direction and substantially continuous in a second direction; an adhesive composition positioned on at least a portion of the first surface of the polymeric matrix; and wherein the polymeric matrix is a breathable film.

21. The conformable adhesive article according to claim 20, wherein the article has a Hand conformability of between approximately 2 and 10 in the first direction.

22. The conformable adhesive article according to claim 20, wherein the article has an inverted moisture vapor transmission rate of at least about 300 g/m²/24 hours.

23. The conformable adhesive article according to claim 20, wherein the article has an upright moisture vapor transmission rate of at least about 300 g/m²/24 hrs.

24. The conformable adhesive article according to claim 20, wherein the plurality of phases retained proximate the film are substantially surrounded by the film.

25. The conformable adhesive article according to claim 24, wherein the plurality of phases substantially surrounded by the film are incompatible with the film.

26. The conformable adhesive article according to claim 20, wherein the plurality of phases comprise a substantially non-elastic material.

27. The conformable adhesive article according to claim 20, wherein the breathable film and the plurality of phases comprise elastomeric materials.

28. The conformable adhesive article according to claim 20, wherein the breathable film is comprised of a material selected from the group consisting of polyurethanes, polyesters, and polyether block amides.

29. The conformable adhesive article according to claim 20, wherein the breathable film is comprised of a polyurethane.

30. The conformable adhesive article according to claim 20, wherein the breathable film and the plurality of phases are produced by coextrusion.

31. The conformable adhesive article according to claim 20, wherein the polymeric matrix material is solvent cast onto a release sheet.

32. The conformable adhesive article according to claim 20, wherein the article comprises a roll good.

33. The conformable adhesive article according to claim 20, wherein the roll good is perforated to form individual lengths of sterile medical dressings.

* * * * *

UNITED STATES PATENT AND TRADEMARK OFFICE
CERTIFICATE OF CORRECTION

| | | |
|---|---|---|
| PATENT NO. | : 6,927,315 B1 | Page 1 of 2 |
| APPLICATION NO. | : 09/364506 | |
| DATED | : August 9, 2005 | |
| INVENTOR(S) | : Steven B. Heinecke | |

It is certified that error appears in the above-identified patent and that said Letters Patent is hereby corrected as shown below:

Title Page
Page 2, Col. 2, under FOREIGN PATENT DOCUMENTS, Line 1, has been repeated with out class/subclass, delete the duplicate line.

Page 2, Col. 2, under FOREIGN PATENT DOCUMENTS, line 3 and 4. Reference has been duplicated, delete duplicate entry on line four. Also insert asterisk from deleted line 4, to line above it.

Column 3
Line 53, after "and the" delete "is".

Column 4
Line 15, after "09/365,286" insert --, Attorney Docket No. 54324USA4A, --.

Column 7
Line 55-56, after "09/365,286," insert -- Attorney Docket No. 54324USA4A, --.

Column 12
Line 56, after "09/325,963," insert -- Attorney Docket No. 54664USA4A, --.

Column 13
Line 5, delete "as-dyes" and insert -- as dyes --, therefore.

Column 14
Line 53, delete "strearns" and insert -- streams --, therefore.

UNITED STATES PATENT AND TRADEMARK OFFICE
CERTIFICATE OF CORRECTION

PATENT NO. : 6,927,315 B1
APPLICATION NO. : 09/364506
DATED : August 9, 2005
INVENTOR(S) : Steven B. Heinecke It is certified that error appears in the above-identified patent and that said Letters Patent is hereby corrected as shown below:

Column 16
Line 36, after "09/365,286," insert -- Attorney Docket No. 54324USA4A, --.
Line 52, after "(1.25-inch)" delete "-".

Signed and Sealed this

Fourth Day of December, 2007

JON W. DUDAS
*Director of the United States Patent and Trademark Office*